(12) United States Patent
Wiklund et al.

(10) Patent No.: US 9,689,823 B2
(45) Date of Patent: Jun. 27, 2017

(54) STEAM QUALITY METER AND MEASUREMENT METHOD

(71) Applicant: Rosemount Inc., Chanhassen, MN (US)

(72) Inventors: David Eugene Wiklund, Eden Prairie, MN (US); Dale Scott Davis, Prior Lake, MN (US)

(73) Assignee: Rosemount Inc., Shakopee, MN (US)

( * ) Notice: Subject to any disclaimer, the term of this patent is extended or adjusted under 35 U.S.C. 154(b) by 79 days.

(21) Appl. No.: 14/643,819

(22) Filed: Mar. 10, 2015

(65) Prior Publication Data
US 2016/0266060 A1    Sep. 15, 2016

(51) Int. Cl.
*G01N 27/22*    (2006.01)

(52) U.S. Cl.
CPC ......... *G01N 27/223* (2013.01); *G01N 27/226* (2013.01)

(58) Field of Classification Search
CPC .................... G01N 27/223; G01N 27/226
USPC ........................................................ 324/664
See application file for complete search history.

(56) References Cited

U.S. PATENT DOCUMENTS

| | | |
|---|---|---|
| 4,137,462 A | 1/1979 | Wyler |
| 4,149,403 A | 4/1979 | Muldary et al. |
| 4,385,661 A | 5/1983 | Fox |
| 4,644,479 A | 2/1987 | Kemper et al. |
| 4,658,208 A | 4/1987 | Lee et al. |
| 4,753,106 A | 6/1988 | Brenner et al. |
| 4,769,593 A * | 9/1988 | Reed .................. F22B 35/16 324/668 |
| 4,849,687 A | 7/1989 | Sims et al. |
| 4,849,988 A | 7/1989 | Chien |
| 4,854,725 A * | 8/1989 | Sims .................. G01N 27/226 324/690 |
| 5,383,024 A | 1/1995 | Maxey et al. |
| 6,128,079 A | 10/2000 | McCloskey et al. |
| 6,587,754 B2 | 7/2003 | Hung et al. |
| 6,591,166 B1 | 7/2003 | Millett et al. |
| 6,992,494 B2 | 1/2006 | Kaiser et al. |
| 7,034,302 B2 | 4/2006 | Davidson et al. |
| 8,325,049 B2 | 12/2012 | Deacon |
| 8,407,027 B2 | 3/2013 | Myougan et al. |
| 2014/0311251 A1 | 10/2014 | Hutchinson |

FOREIGN PATENT DOCUMENTS

EP    1770716 A2    4/2007

OTHER PUBLICATIONS

International Search Report and Written Opinion from PCT Application Serial No. PCT/US2016/017296, dated May 13, 2016, 13 pages.

* cited by examiner

*Primary Examiner* — Billy Lactaoen
(74) *Attorney, Agent, or Firm* — Kinney & Lange, P.A.

(57) ABSTRACT

A steam quality meter includes a pipe with an inlet and an outlet. A rod is located within the pipe between the inlet and the outlet. The rod defines an annular flow passage between an outer wall of the rod and an inner wall of the pipe. A mixing device is located within the pipe between the inlet and an upstream end of the rod. Spaced sensors are located within the annular flow passage. Each sensor is configured to sense capacitance and/or impedance of steam flowing through the annular flow passage.

20 Claims, 3 Drawing Sheets

US 9,689,823 B2

STEAM QUALITY METER AND MEASUREMENT METHOD

BACKGROUND

The present disclosure relates generally to steam quality meters, and in particular, to steam quality meters with electrodes for sensing capacitance and/or impedance.

Steam is commonly used for heating purposes in the process industry and as an injection fluid for recovering hydrocarbons in the oil and gas industry. Steam flow applications such as these utilize saturated steam, which can be all vapor, all liquid, or a combination of vapor and liquid. Thermodynamic relationships use steam quality to calculate properties of saturated steam, such as density and mass flow rate and enthalpy flow rate. These thermodynamic relationships assume that the saturated steam is a homogenous mixture of liquid and vapor phases coexisting at the saturation pressure and temperature, but in practice, saturated steam is rarely completely mixed. Therefore, a device such as a Venturi is used to mix the fluid so that homogeneity can be assumed. The thermodynamic relationships also assume a known steam quality. Density and mass flow rate calculations are often performed assuming a steam quality of 1.0, or 100%. However, for steam quality from 0.9 to 1.0, for every 1% reduction in steam quality, the density of homogenous steam increases by roughly 1%. As steam quality further decreases, the increase in density for every 1% decrease in quality becomes larger. Thus, assuming an incorrect steam quality can result in significant errors when calculating mass flow rate.

At a given pressure, the temperature of a steam mixture remains constant at the saturation temperature until all of the vapor becomes liquid or all of the liquid becomes vapor. Therefore steam quality cannot be determined by only measuring temperature and pressure. As a result, steam quality meters use means such as light, capacitance, impedance, or other methods to determine steam quality. Capacitance of the steam mixture varies with the percentage of liquid water in the mixture. The quality of the mixture is determined under the assumption that water droplets remain uniformly suspended in the vapor as the steam flow passes through horizontal pipe sections. To achieve a uniform homogeneous distribution of water droplets, a mixing device (such as a Venturi, a nozzle, a perforated plate, a swirling device, or other such element) is used. However, water droplets may settle disproportionately at the bottom of a steam pipe or towards the downstream end of the pipe as a steam mixture travels through the pipe. Current steam quality meters do not account for settling of water droplets.

SUMMARY

A steam quality meter includes a pipe with an inlet and an outlet. A rod is located within the pipe between the inlet and the outlet. The rod defines an annular flow passage between an outer wall of the rod and an inner wall of the pipe. A mixing device is located within the pipe between the inlet and an upstream end of the rod. Spaced sensors are located within the annular flow passage. Each sensor is configured to sense capacitance and/or impedance of steam flowing through the annular flow passage.

A method of measuring steam quality includes directing steam into a pipe through an inlet of the pipe, homogenizing the steam, and flowing the steam through an annular flow passage to an outlet of the pipe. The method further includes sensing capacitance and/or impedance of the steam flowing through the annular flow passage at locations within the annular flow passage and producing a steam quality value of the steam flowing through the annular flow passage based upon the capacitance and/or impedance sensed at each of the locations within the annular flow passage.

DETAILED DESCRIPTION

In general, the present disclosure is a steam quality meter with diagnostic capabilities. The steam quality meter has multiple electrodes located on a rod within an annular flow passage within a pipe. The electrodes comprise a sensing structure that allows the steam quality meter to measure steam quality based on the dielectric properties of water droplets suspended in the vapor phase flowing primarily horizontally through the annular flow passage in the pipe. Multiple electrodes are placed along the rod concentrically located within the pipe to allow for multiple capacitance and/or impedance measurements along the axis of flow. These measurements are used to test and verify the assumption of uniform dielectric properties of the fluid mixture along the annular flow passage and therefore improve the confidence in and reliability of the steam quality measurement.

Figure 1:
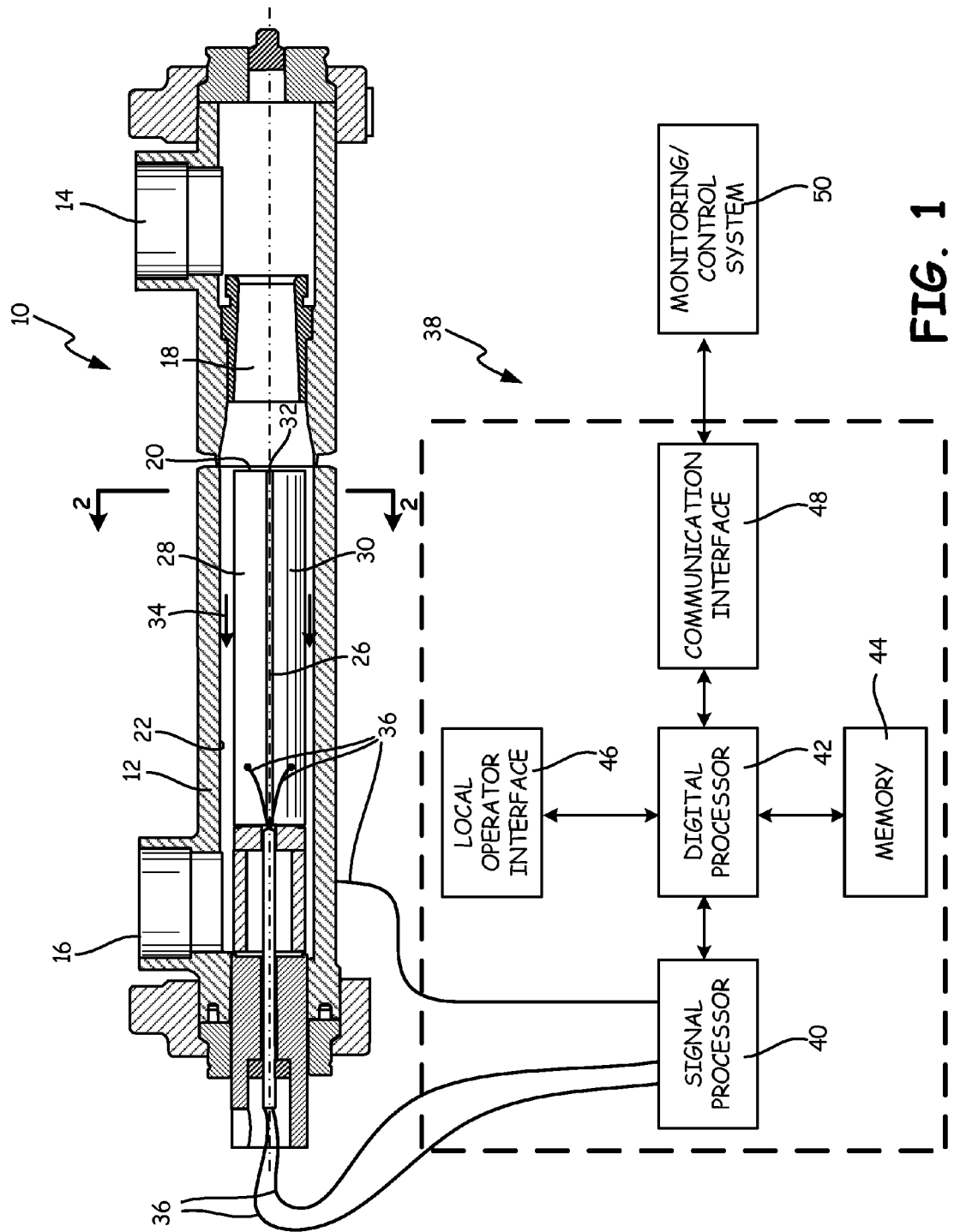
FIG. 1 is a partial side-sectional view of a steam quality meter with an upper electrode and a lower electrode on an inner rod, along with a schematic view of associated electronics for signal processing.
Figure 2A:
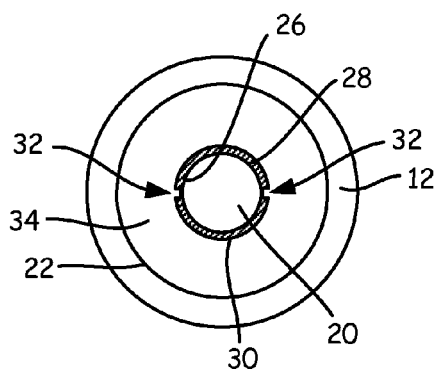
FIG. 2A is a cross-sectional view of the steam quality meter of FIG. 1 along section 2-2 in FIG. 1.

FIG. 1 is a partial side sectional view of steam quality meter 10 according to one embodiment. FIG. 2A is a cross-sectional view along line 2-2 of FIG. 1. As shown in FIGS. 1 and 2A, steam quality meter 10 includes pipe 12 with inlet 14 and outlet 16, mixing device 18, and rod 20. Mixing device 18 and rod 20 are concentrically located within pipe 12. Mixing device 18 can be a Venturi, a nozzle, a perforated plate, a swirling device, or any other suitable mixing device. Pipe 12 includes inner wall 22. In the embodiment shown, pipe 12 is an electrode and can be any conductive material, such as carbon steel. Rod 20 includes outer wall 26 with rod electrodes 28 and 30. In the embodiment shown, rod 20 can be any nonconductive material, such as a ceramic, and rod electrodes 28 and 30 can be any conductive material, such as carbon steel or stainless steel. Rod electrodes 28 and 30 are separated by gaps 32. In the embodiment shown, rod electrodes 28 and 30 are attached to outer wall 26 and gaps 32 represent portions of exposed outer wall 26 that electrically separate rod electrodes 28 and 30. This structure creates two sensors, or coaxial capacitors, one sensor formed by pipe 12 and rod electrode 28 and another sensor formed by pipe 12 and rod electrode 30. In an alternative embodiment, gaps 32 may be filled with a nonconductive material, such as a ceramic material. The space between rod 20 and pipe 12 creates annular flow passage 34.

In this embodiment, wires 36 connect pipe 12 and rod electrodes 28 and 30 to electronics 38. Wires 36 include a wire for each rod electrode 28 and 30, as well as a wire for pipe 12. Electronics 38 can include signal processor 40, digital processor 42, local operator interface 46, memory 44, and communication interface 48. Communication interface 48 can be connected to monitoring/control system 50. Steam quality meter 10 can provide a steam quality measurement output to monitoring/control system 50. The capacitors formed by pipe 12 and rod electrodes 28 and 30 generate an electrical signal, which is carried by wires 36 to signal processor 40. The electrical signal is transmitted to digital processor 42, where the signal is stored in memory 44 and can be displayed at local operator interface 46. The signal can then be transmitted to communication interface 48 and monitoring/control system 50. In alternative embodiments, electronics 38 can be a telemetry system or a supervisory control and data acquisition (SCADA) system. In another alternative embodiment, steam quality meter 10 can be a stand-alone device monitored via local operator interface 46.

In order to measure steam quality, a steam mixture flows into pipe 12 through inlet 14 and through mixing device 18. Mixing device 18 atomizes the liquid part of the fluid into small, uniform droplets in order to generate a homogenous mixture. The homogenous mixture leaves mixing device 18 and enters annular flow passage 34. The mixture exits pipe 12 through outlet 16. When a steam mixture is flowing through annular flow passage 34, the sensors formed between rod electrodes 28 and 30 and pipe 12 determine the dielectric properties of the mixture by measuring capacitance and/or impedance. Upper rod electrode 28 and pipe 12 each act as plates of a first capacitor and thus together sense the capacitance and/or impedance of the steam in the upper half of annular flow passage 34. Lower rod electrode 30 and pipe 12 each act as plates of a second capacitor and thus sense the capacitance and/or impedance of the steam mixture in the lower half of annular flow passage 34. Therefore, steam quality meter 10 takes two measurements of capacitance and/or impedance of the steam passing through annular flow passage 34.

In the embodiment shown, the capacitance and/or impedance measurements can be transmitted through wires 36 to signal processor 40. Signal processor 40 converts the sensed capacitances and/or impedances to digital capacitance and/or impedance values. Digital processor 42 uses the digital values to calculate a steam quality measurement value. For example, digital processor 42 can average the capacitance and/or impedance measurements to calculate an overall steam quality value. Averaging multiple capacitance and/or impedance values is advantageous, because taking the average results in a more accurate steam quality value than the value resulting from taking a single measurement with steam quality meter 10. The steam quality value can be stored in memory 44, displayed on local operator interface 46, and transmitted to a communication interface 48 to monitoring/control system 50 where it can be displayed. In alternative embodiments, a telemetry system or SCADA system can process the capacitance and impedance measurements to determine and/or output steam quality diagnostic information. The steam quality value can be displayed as a percentage. A 100% quality indicates that the fluid flowing through annular flow passage 34 is entirely vapor. A 0% quality indicates that the fluid flowing through annular flow passage 34 is entirely liquid.

In addition to providing an overall steam quality value, the two capacitance and/or impedance measurements can also be displayed or separately analyzed by digital processor 42 in order to display a steam quality value for the upper half of annular flow passage 34 and a steam quality value for the lower half of annular flow passage 34. This allows the user to evaluate differences in the steam mixture flowing through the upper half of annular flow passage 34 and the lower half of annular flow passage 34. The separate capacitance and/or impedance measurements can also provide an indication of the reliability of the overall steam quality value. For example, if the capacitance measurement for the upper half of annular flow passage 34 is lower than the capacitance measurement for the lower half of annular flow passage 34, this could indicate that settling is occurring in the bottom half of annular flow passage 34 or that the flow rate of the mixture has dropped off. A significant difference in the two separate measurements can alert the user to adjust flow rate or pipe size in order to maintain the quality of the mixture. Multiple capacitance and/or impedance measurements are also advantageous, because multiple measurements allow for redundancy.

Figure 2B:
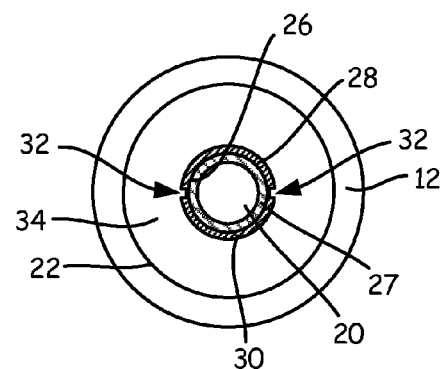
FIG. 2B is a cross-sectional view of an alternative embodiment of the steam quality meter of FIG. 1 along section 2-2 of FIG. 1.

FIG. 2B is a cross-sectional view of an alternative embodiment of steam quality meter 10 along line 2-2 of FIG. 1. Steam quality meter 10 includes pipe 12 and rod 20. Pipe 12 includes inner wall 22. In the embodiment shown, pipe 12 is an electrode and can be any conductive material, such as carbon steel. Rod 20 includes insulating layer 27 and outer wall 26 with rod electrodes 28 and 30. In the embodiment shown, rod 20 can be made of a conductive material surrounded by insulating layer 27. Insulating layer 27 can be made of any nonconductive material, such as a ceramic. Rod electrodes 28 and 30 can be any conductive material, such as carbon steel or stainless steel. Rod electrodes 28 and 30 are separated by gaps 32. In the embodiment shown, rod electrodes 28 and 30 are attached to outer wall 26 and gaps 32 represent portions of exposed outer wall 26 that electrically separate rod electrodes 28 and 30. This structure creates two sensors, or coaxial capacitors, one sensor formed by pipe 12 and rod electrode 28 and a sensor formed by pipe 12 and rod electrode 30. In an alternative embodiment, gaps 32 may be filled with a nonconductive material, such as a ceramic material. The space between rod 20 and pipe 12 creates annular flow passage 34.

Figure 2C:
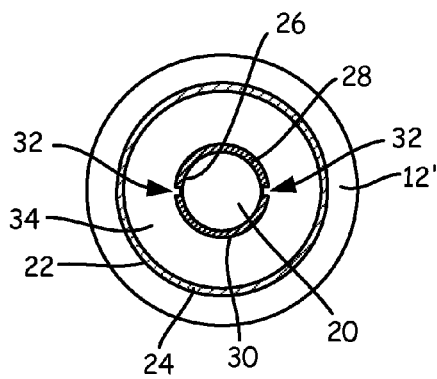
FIG. 2C is a cross-sectional view of an alternative embodiment of the steam quality meter of FIG. 1 along section 2-2 of FIG. 1.

FIG. 2C is a cross-sectional view of an alternative embodiment of steam quality meter 10 along line 2-2 of FIG. 1. Steam quality meter 10 includes pipe 12' and rod 20. Pipe 12' includes inner wall 22 with pipe electrode 24. In the embodiment shown, pipe 12' can be a nonconductive material, such as a ceramic, and pipe electrode 24 can be any conductive material, such as carbon steel. Rod 20 includes outer wall 26 with rod electrodes 28 and 30. In the embodiment shown, rod 20 can be any nonconductive material, such as a ceramic, and rod electrodes 28 and 30 can be any conductive material, such as carbon steel or stainless steel. Rod electrodes 28 and 30 are separated by gaps 32. In the embodiment shown, rod electrodes 28 and 30 are attached to outer wall 26 and gaps 32 represent portions of exposed outer wall 26 that electrically separate rod electrodes 28 and 30. This structure creates two sensors, or coaxial capacitors, one sensor formed by pipe electrode 24 and rod electrode 28 and a sensor formed by pipe electrode 24 and rod electrode 30. In an alternative embodiment, gaps 32 may be filled with a nonconductive material, such as a ceramic material. The space between rod 20 and pipe 12' creates annular flow passage 34.

Figure 2D:
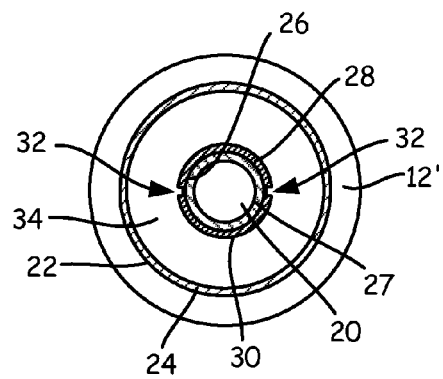
FIG. 2D is a cross-sectional view of an alternative embodiment of the steam quality meter of FIG. 1 along section 2-2 of FIG. 1.

FIG. 2D is a cross-sectional view of an alternative embodiment of steam quality meter 10 along line 2-2 of FIG. 1. Steam quality meter 10 includes pipe 12' and rod 20. Pipe 12' includes inner wall 22 with pipe electrode 24. In the embodiment shown, pipe 12' can be a nonconductive material, such as a ceramic, and pipe electrode 24 can be any conductive material, such as carbon steel. Rod 20 includes insulating layer 27 and outer wall 26 with rod electrodes 28 and 30. In the embodiment shown, rod 20 can be made of a conductive material surrounded by insulating layer 27. Insulating layer 27 can be made of any nonconductive material, such as a ceramic. Rod electrodes 28 and 30 can be any conductive material, such as carbon steel or stainless steel. Rod electrodes 28 and 30 are separated by gaps 32. In the embodiment shown, rod electrodes 28 and 30 are attached to outer wall 26 and gaps 32 represent portions of exposed outer wall 26 that electrically separate rod electrodes 28 and 30. This structure creates two sensors, or coaxial capacitors, one sensor formed by pipe electrode 24 and rod electrode 28 and a sensor formed by pipe electrode 24 and rod electrode 30. In an alternative embodiment, gaps 32 may be filled with a nonconductive material, such as a ceramic material. The space between rod 20 and pipe 12' creates annular flow passage 34.

Figure 3:
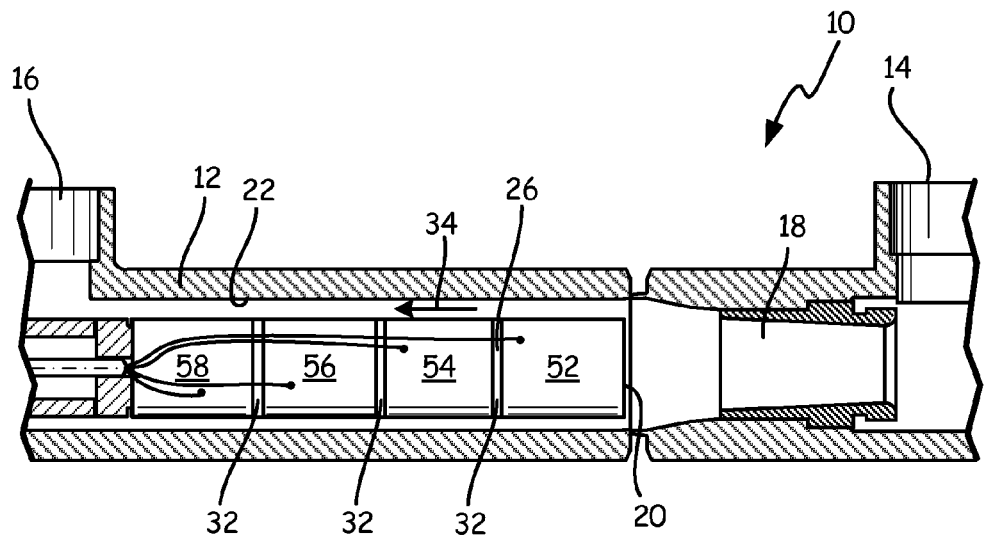
FIG. 3 is a partial side-sectional view of the steam quality meter of FIG. 1 with longitudinally spaced electrodes on the inner rod.

According to another embodiment, FIG. 3 is a partial side-sectional view of steam quality meter 10 with longitudinally spaced rod electrodes 52, 54, 56, and 58 attached to outer wall 26 of rod 20 instead of rod electrodes 28 and 30 attached to outer wall 26 of rod 20. Rod electrodes 52, 54, 56, and 58 are electrically separated by gaps 32, which represent portions of exposed outer wall 26. In an alternative embodiment, gaps 32 can be filled with an insulating material such as a ceramic. This structure creates four sensors, or coaxial capacitors. A first sensor is formed by pipe 12 and rod electrode 52. Second, third, and fourth sensors are formed downstream of the first sensor by pipe 12, and rod electrodes 54, 56, and 58, respectively. In alternative embodiments, the four sensors can be created with alternative configurations of pipe 12 and rod 20, as shown in FIGS. 2B-2D.

In this embodiment, rod electrode 52 and pipe 12 each act as plates of a first capacitor and thus together sense the capacitance and/or impedance of the steam mixture flowing through annular flow passage 34 in a first portion of annular flow passage 34. Rod electrodes 54, 56, and 58 along with pipe 12 act as plates of second, third, and fourth capacitors for sensing the capacitance and/or impedance of steam flowing through annular flow passage 34 in second, third, and fourth portions of annular flow passage 34. Therefore, in the embodiment shown in FIG. 3, steam quality meter 10 takes four measurements of capacitance and/or impedance of the steam passing through annular flow passage 34. In alternate embodiments, any number of longitudinally spaced rod electrodes can be attached to outer wall 26 of rod 20 to provide any number of measurements of capacitance and/or impedance.

The capacitance and/or impedance measurements can be averaged and processed by electronics 38 and an overall steam quality measurement can be displayed by monitoring/control system 50, as discussed above with reference to FIGS. 1 and 2A. The capacitance and/or impedance measurements taken by the embodiment shown in FIG. 3 can be separately analyzed in an algorithm to evaluate differences in the steam mixture as the mixture flows downstream through annular flow passage 34. The separate capacitance and/or impedance measurements can also provide an indication of the reliability of the overall steam quality value. For example, if the capacitance measurement for the first portion of annular flow passage 34 is lower than the capacitance measurement for the second, downstream portion of annular flow passage 34, this could indicate that settling is occurring as the steam mixture flows downstream through flow passage 34 or that the flow rate of the steam mixture has dropped off. A significant difference in separate measurements can alert the user to adjust flow rate or pipe size in order to maintain the quality of the steam. Multiple capacitance/and or impedance measurements are also advantageous, because multiple measurements allow for redundancy.

Figure 4:
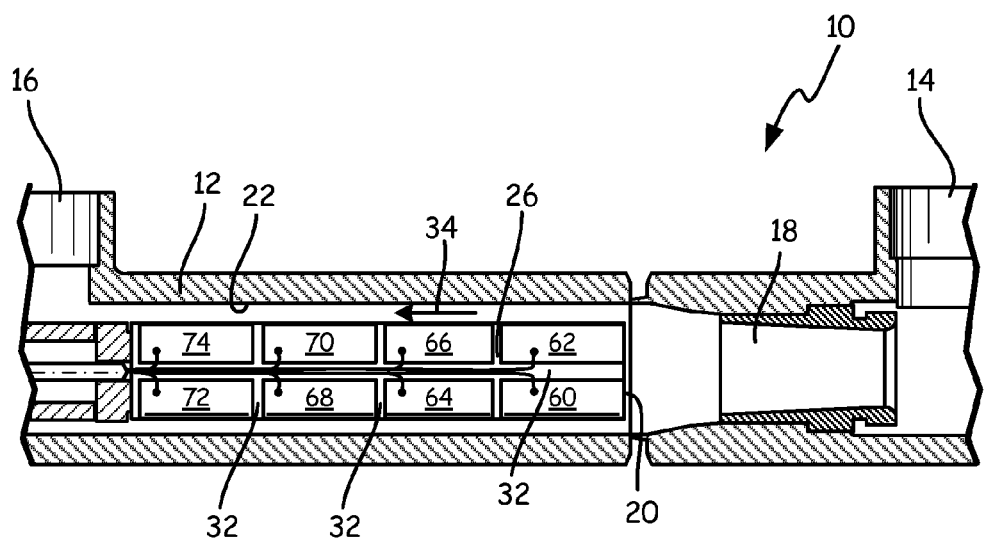
FIG. 4 is a partial side-sectional view of the steam quality meter of FIG. 1 with longitudinally spaced upper and lower electrodes on the inner rod.

FIG. 4 is a partial side-sectional view of another embodiment of steam quality meter 10 with rod electrodes 60, 62, 64, 66, 68, 70, 72, and 74 attached to outer wall 26 of rod 20 instead of rod electrodes 28 and 30 attached to outer wall 26 of rod 20. Rod electrodes 62, 66, 70, and 74 are longitudinally spaced and attached to an upper half of outer wall 26. Rod electrodes 60, 64, 68, and 72 are longitudinally spaced and attached to a lower half of outer wall 26. Rod electrodes 60, 62, 64, 66, 68, 70, 72, and 74 are electrically separated by gaps 32, which represent portions of exposed outer wall 26. In an alternative embodiment, gaps 32 can be filled with an insulating material such as a ceramic. This structure creates eight sensors, or coaxial capacitors. A first sensor on the upper half of outer wall 26 is formed by pipe 12 and rod electrode 62. Second, third, and fourth sensors are formed downstream of the first sensor by pipe 12 and rod electrodes 66, 70, and 74, respectively. A fifth sensor on the lower half of outer wall 26 is formed by pipe 12 and rod electrode 60. Sixth, Seventh, and eighth sensors are formed downstream of the first sensor by pipe 12 and rod electrodes 64, 68, and 72, respectively. In alternative embodiments, the eight sensors can be created with alternative configurations of pipe 12 and rod 20, as shown in FIGS. 2B-2D.

Rod electrode 62 and pipe 12 each act as plates of a first capacitor and thus together sense the capacitance and/or impedance of the steam mixture flowing through annular flow passage 34 in an upper half of a first portion of annular flow passage 34. Rod electrodes 66, 70, and 74 along with pipe 12 act as plates of second, third, and fourth capacitors for sensing the capacitance and/or impedance of the steam mixture flowing through the upper half of annular flow passage 34 in second, third, and fourth portions of annular flow passage 34. Rod electrode 60 and pipe 12 each act as plates of a fifth capacitor and thus together sense the capacitance and/or impedance of steam flowing through annular flow passage 34 in a lower half of the first portion of annular flow passage 34. Rod electrodes 64, 68, and 72 along with pipe 12 act as plates of sixth, seventh, and eighth capacitors for sensing the capacitance and/or impedance of steam flowing through the lower half of annular flow passage 34 in the second, third, and fourth portions of annular flow passage 34. Therefore, in the embodiment shown in FIG. 3, steam quality meter 10 takes eight measurements of capacitance and/or impedance of the steam mixture passing through annular flow passage 34. In alternate embodiments, any number of longitudinally spaced rod electrodes can be attached to the upper and lower halves of outer wall 26 of rod 20 to provide any number of measurements of capacitance and/or impedance.

The capacitance and/or impedance measurements can be averaged and processed by electronics 38 and an overall steam quality measurement can be displayed by monitoring/ control system 50, as discussed above with reference to FIGS. 1 and 2A. The capacitance and/or impedance measurements taken by the embodiment shown in FIG. 4 can be separately analyzed in an algorithm to evaluate differences in the steam mixture as the mixture flows downstream through annular flow passage 34 as well as differences in the steam mixture flowing through the upper and lower halves of annular flow passage 34. The separate capacitance and/or impedance measurements can also provide an indication of the reliability of the overall steam quality value. For example, if the capacitance measurement for the upper half of the first portion of annular flow passage 34 is lower than the capacitance measurement for the upper half of the second, downstream portion of annular flow passage 34, this could indicate that settling is occurring as the steam mixture flows downstream through the upper half of flow passage 34 or that the flow rate of the steam mixture has dropped off. A significant difference in separate measurements can alert the user to adjust flow rate or pipe size in order to maintain the quality of the steam. Multiple capacitance/and or impedance measurements are also advantageous, because multiple measurements allow for redundancy.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A steam quality meter comprising:
   a pipe having an inlet and an outlet;
   a rod located within the pipe between the inlet and the outlet and defining an annular flow passage between an outer wall of the rod and an inner wall of the pipe;
   a mixing device within the pipe between the inlet and an upstream end of the rod; and
   a plurality of spaced sensors within the annular flow passage, wherein the plurality of spaced sensors includes at least one upper sensor configured to sense capacitance and/or impedance of steam flowing through an upper half of the annular flow passage, and wherein the plurality of spaced sensors includes at least one lower sensor configured to sense capacitance and/or impedance of steam flowing through a lower half of the annular flow passage.

2. The steam quality meter of claim 1, wherein the plurality of sensors comprises a plurality of electrodes.

3. The steam quality meter of claim 2, wherein the plurality of electrodes includes a plurality of rod electrodes at the outer wall of the rod and at least one pipe electrode.

4. The steam quality meter of claim 3, wherein the pipe comprises a conductive material and the pipe is the pipe electrode.

5. The steam quality meter of claim 3, wherein the pipe comprises an insulating material.

6. The steam quality meter of claim 5, wherein the pipe electrode is attached to the inner wall of the pipe.

7. The steam quality meter of claim 3, wherein the plurality of rod electrodes includes an electrode at an upper half of the outer wall of the rod and an electrode at a lower half of the outer wall of the rod.

8. The steam quality meter of claim 3, wherein the plurality of rod electrodes includes longitudinally spaced electrodes at the outer wall of the rod.

9. The steam quality meter of claim 3, wherein the plurality of rod electrodes includes longitudinally spaced electrodes at an upper half of the outer wall of the rod and longitudinally spaced electrodes at a lower half of the outer wall of the rod.

10. The steam quality meter of claim 3, wherein the rod includes an insulating layer.

11. The steam quality meter of claim 3, wherein at least one gap separates the electrodes of the plurality of rod electrodes.

12. The steam quality meter of claim 11, wherein the at least one gap is filled with an insulating material.

13. The steam quality meter of claim 1, and further comprising circuitry for measuring and outputting a steam quality value of the steam flowing through the annular flow passage based upon the capacitance and/or impedance sensed by each of the plurality of sensors.

14. The steam quality meter of claim 13, wherein the circuitry comprises a supervisory control and data acquisition system or a telemetry system.

15. The steam quality meter of claim 14, wherein the circuitry includes a local operator interface.

16. A method of measuring steam quality, the method comprising:
    directing steam into a pipe through an inlet of the pipe;
    homogenizing the steam;
    flowing the steam through an annular flow passage within the pipe to an outlet of the pipe;
    sensing capacitance and/or impedance of the steam flowing through an upper half of the annular flow passage at one or more upper locations within the annular flow passage;
    sensing capacitance and/or impendence of the steam flowing through a lower half of the annular flow passage at one or more lower locations within the annular flow passage; and
    producing a steam quality value of the steam flowing through the upper half and the lower half of the annular flow passage based upon the capacitance and/or impedance sensed at each of the upper and lower locations within the annular flow passage at which capacitance and/or impedance is sensed;
    wherein sensing capacitance and/or impedance of the steam includes sensing capacitance and/or impedance of the steam between an electrode at an inner wall of the pipe and a plurality of upper and lower rod electrodes at the outer wall of a rod located within the pipe between the inlet of the pipe and the outlet of the pipe.

17. The method of claim 16, and further comprising comparing the capacitance and/or impedance sensed at each of the upper and lower locations within the annular flow passage to produce an indication of reliability of the steam quality value.

18. The method of claim 16, wherein producing a steam quality value comprises averaging the capacitance and/or impedance at each of the upper and lower locations within the annular flow passage.

19. A method of measuring steam quality, the method comprising:
    directing steam into a pipe through an inlet of the pipe;
    homogenizing the steam;
    flowing the steam through an annular flow passage within the pipe to an outlet of the pipe;

sensing capacitance and/or impedance of the steam flowing through an upper half of the annular flow passage at one or more upper locations within the annular flow passage;
sensing capacitance and/or impendence of the steam flowing through a lower half of the annular flow passage at one or more lower locations within the annular flow passage;
producing a steam quality value of the steam flowing through the upper half and the lower half of the annular flow passage based upon the capacitance and/or impedance sensed at each of the upper and lower locations within the annular flow passage at which capacitance and/or impedance is sensed; and
comparing the capacitance and/or impedance sensed at each of the upper and lower locations within the annular flow passage to produce an indication of reliability of the steam quality value.

20. A method of measuring steam quality, the method comprising:
directing steam into a pipe through an inlet of the pipe;
homogenizing the steam;
flowing the steam through an annular flow passage within the pipe to an outlet of the pipe;
sensing capacitance and/or impedance of the steam flowing through an upper half of the annular flow passage at one or more upper locations within the annular flow passage;
sensing capacitance and/or impendence of the steam flowing through a lower half of the annular flow passage at one or more lower locations within the annular flow passage; and
producing a steam quality value of the steam flowing through the upper half and the lower half of the annular flow passage based upon the capacitance and/or impedance sensed at each of the upper and lower locations within the annular flow passage at which capacitance and/or impedance is sensed;
wherein producing a steam quality value comprises averaging the capacitance and/or impedance at each of the upper and lower locations within the annular flow passage.

* * * * *